United States Patent [19]
Laurent et al.

[11] Patent Number: 5,469,857
[45] Date of Patent: Nov. 28, 1995

[54] APPARATUS FOR MEASURING ELECTRICAL ACTIVITY IN THE HEART WITH GRAPHICAL DISPLAY OF ELECTRODE CONTACT WITH TISSUE

[75] Inventors: Estan Laurent, Vikbolandet; Monica Magnusson, Lidingoe, both of Sweden

[73] Assignee: Siemens Elema AB, Solna, Sweden

[21] Appl. No.: 198,587

[22] Filed: Feb. 18, 1994

[30] Foreign Application Priority Data

Mar. 12, 1993 [SE] Sweden ............................. 93008258

[51] Int. Cl.$^6$ ........................................ A61B 5/04
[52] U.S. Cl. ............................. 128/710; 128/696
[58] Field of Search ..................... 128/668, 670, 128/695, 696, 700, 702, 710, 733, 734

[56] References Cited

U.S. PATENT DOCUMENTS 3,994,286 11/1976 Svensson .
4,023,565 5/1977 Ohlsson .
4,213,465 7/1980 Reinheim .
4,235,246 11/1980 Weiss .
4,245,643 1/1981 Benzing, III et al. .
5,085,224 2/1992 Galen et al. .
5,282,840 2/1994 Hudrlik ................................. 128/734

Primary Examiner—William E. Kamm
Assistant Examiner—Marianne Parker
Attorney, Agent, or Firm—Hill, Steadman & Simpson

[57] ABSTRACT

An apparatus for measuring electrical activity in the heart, such as an ECG apparatus, has an input amplifier with multiple inputs to which the respective poles of electrodes introduced into a patient are intended to be connected. The input amplifier includes a sensing stage for sensing the impedance across the amplifier inputs after connection of the electrodes, in order to identify the poles which are in contact with the patient's heart. A display is connected to the input amplifier to graphically indicate which electrode poles are connected, and which are in contact with the heart.

8 Claims, 3 Drawing Sheets

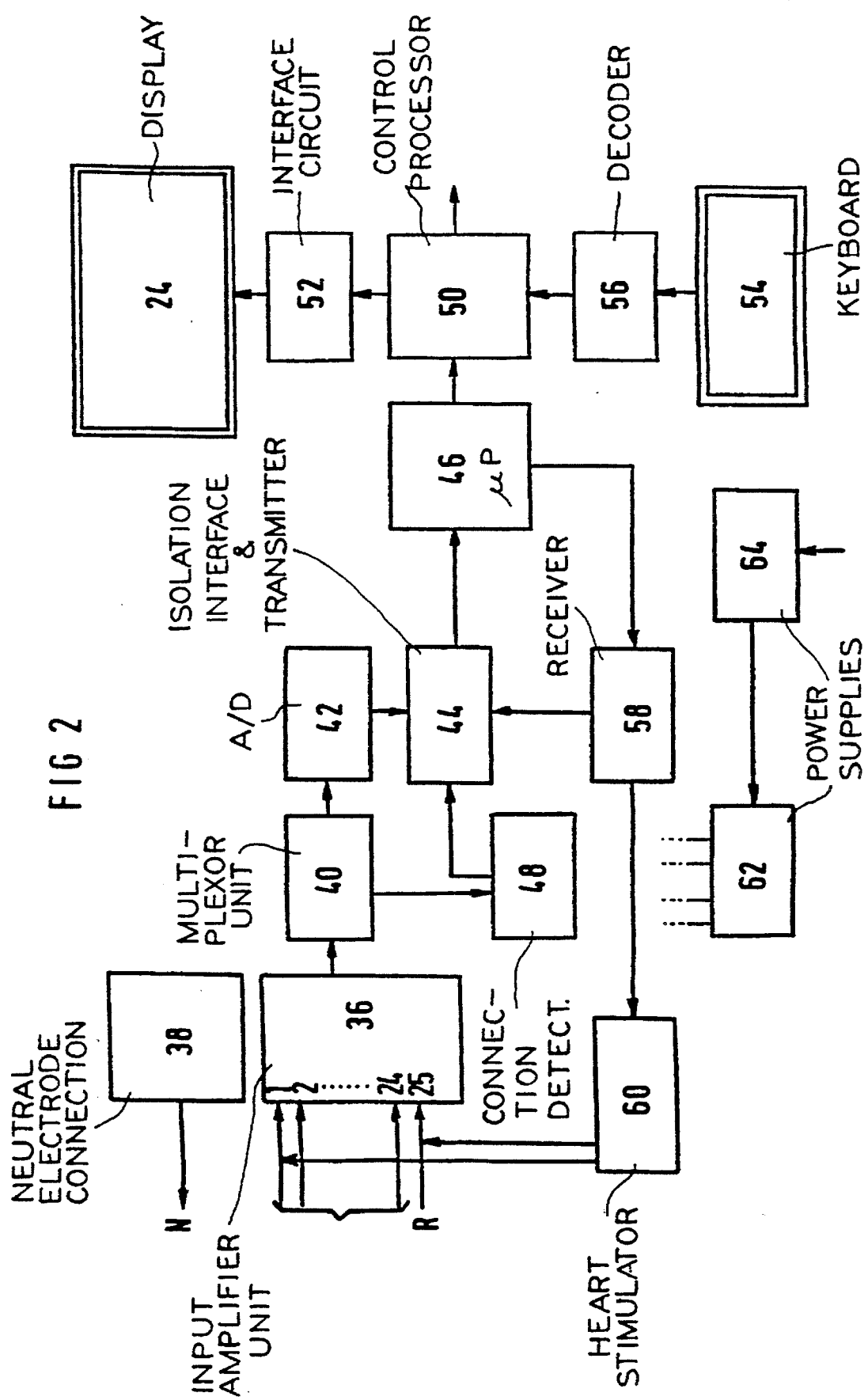

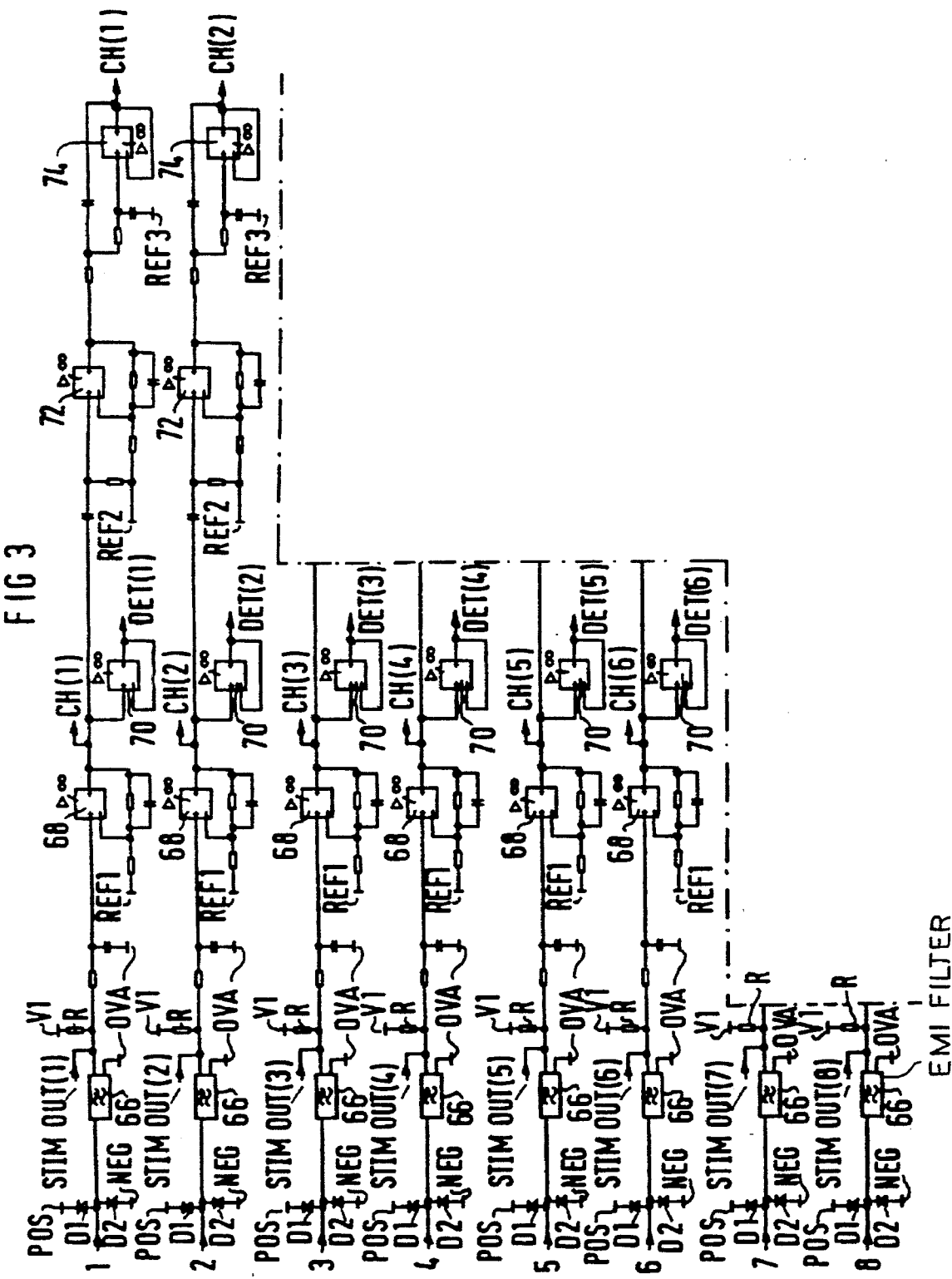

5,469,857

APPARATUS FOR MEASURING ELECTRICAL ACTIVITY IN THE HEART WITH GRAPHICAL DISPLAY OF ELECTRODE CONTACT WITH TISSUE

BACKGROUND OF THE INVENTION

1. Field of the Invention

The present invention is directed to an apparatus for measuring in vivo electrical activity in a heart, of the type having an input amplifier unit having a plurality of inputs to which poles of electrodes introduced into the patient are intended to be connected.

2. Description of the Prior Art

Devices for processing physiological signals are known, for example, from U.S. Pat. No. 3,994,286 and U.S. Pat. No. 4,023,565. These types of devices are intended for use in generating ECG and EEG recordings, and are specially designed to suppress certain noise signals and to enable a simple realization of the measurement apparatus.

An electroencephalograph apparatus is disclosed in U.S. Pat. No. 4,213,465, having switches arranged in a pattern which reproduces the human head. The measurement electrodes are attached by means of these switches to respective input channels, the position of the switches configured in the representation of the head corresponding to the positions of the electrodes on the patient's head. In this manner, the position of the switches in the rendition of the head provides the operator with a good overview of electrode placement.

SUMMARY OF THE INVENTION

It is an object of the present invention to provide an apparatus for measuring electrical activity in the heart of a patient, wherein the locations at which the electrode poles are connected to the heart is graphically depicted.

It is a further object of the present invention to provide such an apparatus which also graphically displays whether a connection exists for each pole which is intended for connection to the heart.

The above objects are achieved in an apparatus for measuring electrical activity in the heart constructed in accordance with the principles of the present invention, having an input amplifier unit with a plurality of inputs to which poles of electrodes introduced into the patient are intended to be connected. The input amplifier unit includes a sensing stage for sensing the impedance across the amplifier unit inputs after connection of the electrodes, in order to identify the poles which are in contact with the patient's heart. A display is connected to the input amplifier unit to graphically indicate which electrode poles are connected, and which are in contact with the heart.

The apparatus according to the invention is of a type intended for measuring electrical activity in the heart, i.e., IECG. The apparatus measures both spontaneous activity and activity triggered by the apparatus. The apparatus automatically senses which electrode poles are in contact with the heart. This is appropriately depicted on a graphics screen. This graphics screen provides the operator with a good overview of the coupling of the electrode poles to the amplifier unit, shows whether an electrode is connected to the apparatus, and indicates whether a break is present in any of the electrode poles.

In an embodiment of the apparatus of the invention, an analog-to-digital converter having an output terminal connected via an isolation interface to a microprocessor for signal processing, and a following control processor, are employed for controlling the graphical representation of the poles on the display. The isolation interface isolates the patient from other electrical equipment.

In a further embodiment of the apparatus of the invention, a potential sensed by a designated electrode pole serves as a reference voltage for all input amplifiers in the input amplifier unit. For example, the voltage at the first electrode pole which is connected can be employed as a reference for the amplifier units, instead of isolated ground.

In a further embodiment of the invention, a heart stimulator is connected to an optional electrode pole via a switching unit. The apparatus according to the invention can contain a built-in stimulator to save space in the examination room, which usually already contains a large amount of equipment. Measurements wherein cardiac activity is to be triggered by the apparatus can then be undertaken using the built-in stimulator, with an appropriate triggering and sensing sequence being simultaneously programmed in the apparatus. This avoids the necessity of having to separate program, and then coordinate the operation of, a cardiac stimulator and a sensing apparatus. A high degree of flexibility for stimulation modes is achieved by connecting the heart stimulator to optional electrode poles.

In another embodiment of the apparatus of the invention, shunt diodes are connected across the inputs of the input amplifiers of the amplifier unit to protect the input amplifiers against high defibrillation voltages.

DESCRIPTION OF THE DRAWINGS

FIG. 2 is a block diagram of the equipment for recording an IECG shown in FIG. 1.

FIG. 3 is a circuit diagram showing a part of the input amplifier unit in the apparatus of the invention in detail.

DESCRIPTION OF THE PREFERRED EMBODIMENTS

Figure 1:
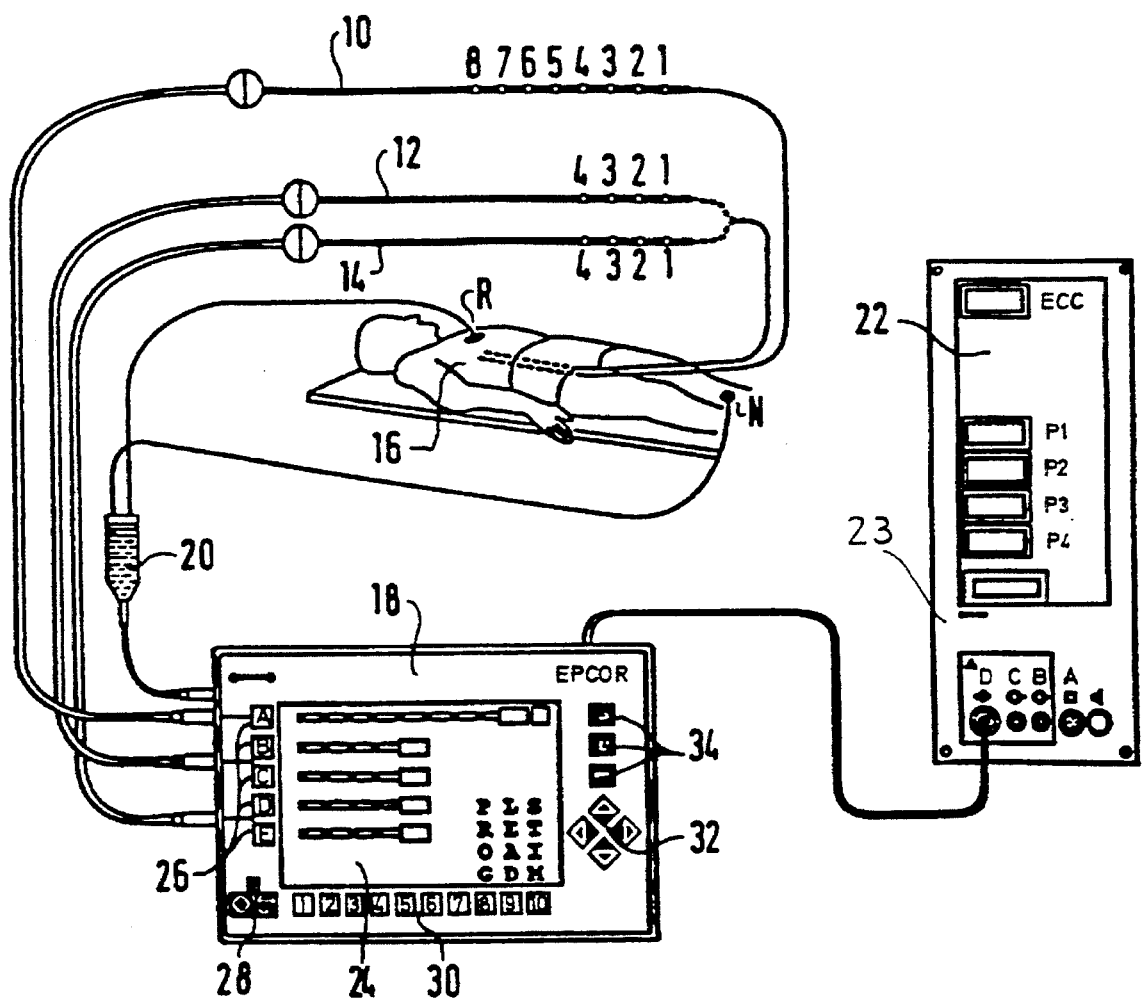
FIG. 1 illustrates the use of a system constructed in accordance with the principles of the present invention for recording an IECG.

The apparatus schematically shown in FIG. 1 includes three electrode catheters 10, 12 and 14 implanted in a patient 16 for measuring electrical activity in the patient's heart, i.e., for making IECG'S recordings. The electrode 10 has eight poles 1–8, and the electrodes 12 and 14 each have four poles 1–4. A reference electrode R and a neutral electrode N are also attached to the patient 16. The reference electrode R is only employed in unipolar measurements.

The electrode catheters 10, 12 and 14, the reference electrode R and the neutral electrode N are connected by appropriate cables to the measurement equipment 18. Cables from the reference electrode R and the neutral electrode N are collected in a junction box 20.

The measurement equipment 18 is connected to the input panel 22 of a programmable recorder 23 for recording measured events. Since the programmable recorder 23 does not form a part of the invention, it will not be described in detail.

The measurement equipment 18 includes a display 24 on which the electrodes 10, 12 and 14 with their respective sets of poles 1–8 and 1–4 can be graphically represented. Each connected electrode 10, 12 and 14 is schematically shown on the screen, and the representation of the respective electrodes 10, 12 and 14 indicates whether each pole thereof is in contact with the heart. Thus, the screen representation provides the operator with clear information as to the electrodes connected to the measurement equipment 18, and whether the poles are in contact with the heart. The operator can thus immediately see whether there is an interruption in any of the electrode poles.

The screen 24 is suitably background lit, since the level of lighting in examination rooms is often low.

Preferably, a built-in heart stimulator is contained within the housing of the measurement equipment 18, which can be connected to optional electrode poles to deliver stimulation pulses to the heart.

The front panel of the measurement equipment 18 further has different operating buttons 26, 28, 30, 32 and 34 for controlling the operation of the apparatus, e.g., for connecting the desired electrode poles, selecting different measurement and stimulation modes, etc.

FIG. 2 shows a block diagram of the measurement equipment 18 of FIG. 1. A total of twenty-four electrode poles, distributed among five catheters, can be connected to the input amplifier unit 36. An input terminal for the reference electrode R is also shown. The equipment also includes a connection 38 for the neutral electrode N.

A multiplexer unit 40, through which the signals from all of the electrode poles are multiplexed to an A/D converter 42, follows the input amplifier unit 36. The A/D-converted signals are transmitted, via an isolation interface and a transmitter 44, to a microprocessor 46 for signal processing. The isolation interface isolates the patient 16 from the electrical equipment on the other side of the isolation interface.

A connection detector 48, which delivers information to the transmitter 44 regarding the electrode poles which are connected, is also connected to the multiplexer 40. The information regarding connection of the electrode poles is forwarded to the signal processor 46. A control processor 50 is connected following the signal processor 46. The control processor 50 controls the display 24 via an interface circuit 52 so that the coupling of the electrode poles is depicted on the display, as described above. The control processor 50 is also connected to the input panel 22 of the recorder 23.

The operating buttons 26, 28, 30, 32 and 34 shown in FIG. 1 are represented in FIG. 2 by the keyboard 54 which is connected via a decoder 56 to the control processor 50, for manually controlling the control processor 50. The signal processor 46 is further connected, via a receiver 58, to a heart stimulator 60 which is connectable, through a stimulation multiplexer in the form of a switching unit, to optional electrode poles. The stimulator 60 is shown in FIG. 2 connected between the electrode pole 1 and the reference pole R for emitting stimulation pulses between these poles.

The stimulator 60 has two synchronized outputs permitting synchronized stimulation in the atrium and in the ventricle of the heart.

The equipment further includes power supplies 62 and 64. The individual connections of the components with the power supply 62 are schematically indicated.

FIG. 3 is a circuit diagram showing a portion of the input amplifier unit 36 with eight inputs for electrode poles.

A so-called EMI filter 66 is provided for each input terminal to protect against external interference, followed by a plurality of substantially identical amplifier stages 68, 70, 72 and 74 for successive amplification of the signal before it is supplied to the multiplexer 40.

If input 1 is not connected to an electrode pole in contact with the heart, i.e., when this input is open and is passing no current, the voltage $V_1$ causes the input to go to a high level via the resistor R. This high level is amplified in the amplifier 68, and is delivered from the amplifier 70 at DET(1) for supply to the connection detector 48, and for a corresponding indication on the screen 24. The same signal, although further amplified in the amplifiers 72 and 74, is fed through the multiplexer 40 to the A/D converter 42 at CH(1).

When the electrode pole connected to the input 1 is in contact with the heart, the input is lowered to a low level (zero level), and the corresponding low signal is supplied to the detector 48 and to the A/D converter 42.

In this manner, an automatic sensing of the poles connected to the heart, and the corresponding screen indications, are achieved.

A voltage can be collected at CH(1) which is appropriate for use as reference voltage REF(1). The same reference voltage is then used for all input channels. Preferably, the voltage CH(1) can be obtained from the first electrode pole which is connected.

The heart stimulator 60 is connectable, via a stimulation multiplexer, to electrode poles via the STIM OUT terminals.

Shunt diodes D1 and D2 are provided at each input to protect the amplifiers against high defibrillation voltages, which may be delivered by the heart stimulator 65. The requisite resistance is obtained in the patient's body between the externally applied patch electrode and the heart.

Although modifications and changes may be suggested by those skilled in the art, it is the intention of the inventors to embody within the patent warranted hereon all changes and modifications as reasonably and properly come within the scope of their contribution to the art.

we claim as our invention:

1. A medical apparatus comprising:

a plurality of electrodes, each electrode having a plurality of poles, at least some of said poles being introducible into patient for contact with the heart of said patient;

an input amplifier unit having a plurality of inputs to which said poles of said plurality of electrodes are respectively connected;

sensing means in said input amplifier unit for sensing an impedance across the inputs of said input amplifier unit after connection of said electrodes thereto for identifying poles which are in contact with the heart; and display means connected to said input amplifier unit for graphically indicating which of said poles are connected to said input amplifier unit and which of said poles are in contact with said heart.

2. An apparatus as claimed in claim 1 wherein said sensing means comprises a voltage source and a resistor, said voltage source being connected through said resistor to each of said amplifier inputs, said resistor having a current therethrough which varies according to the impedance sensed from the input, thereby varying the voltage at the input.

3. An apparatus as claimed in claim 1 further comprising:

multiplexer means connected to said input amplifier unit for multiplexing all of said inputs, said multiplexer means having an output; and an analog-to-digital converter connected to said output of said multiplexer means.

4. An apparatus as claimed in claim 3 wherein said analog-to-digital converter has an output, and further comprising:

an isolation interface and microprocessor means having an input connected via said isolation interface to the output of said analog-to-digital converter for processing signals from each of said inputs; and control processor means connected to said microprocessor means for controlling the graphical representation of said poles on said display means.

5. An apparatus as claimed in claim 1 wherein said input amplifier unit comprises a plurality of input amplifiers, and wherein a potential at a predetermined one of said poles serves as a reference potential for all of said input amplifiers.

6. An apparatus as claimed in claim 1 further comprising a switching Unit and a heart stimulator connectable to any selected one of said poles via said switching unit.

7. An apparatus as claimed in claim 6 wherein said input amplifier unit comprises a plurality of input amplifiers, each input amplifier having an input amplifier input, said apparatus further comprising shunt diodes connected at each of said input amplifier inputs for protecting the respective input amplifiers against high voltages.

8. An apparatus as claimed in claim 1 wherein said electrodes comprise multipolar electrodes.

* * * * *